United States Patent

Feldman et al.

[11] Patent Number: 5,943,127
[45] Date of Patent: Aug. 24, 1999

[54] COINED LINE ANALYZER

[75] Inventors: Sandra Freedman Feldman, Niskayuna; Harsha Mysore Hatti, Schenectady, both of N.Y.

[73] Assignee: General Electric Company, Schenectady, N.Y.

[21] Appl. No.: 09/188,095

[22] Filed: Nov. 9, 1998

[51] Int. Cl.$^6$ ............................................. G01N 21/88
[52] U.S. Cl. ...................... 356/237.2; 356/378; 356/446; 356/73
[58] Field of Search ................... 356/237.2, 371, 356/378, 446, 73; 73/81

[56] References Cited

U.S. PATENT DOCUMENTS

| | | |
|---|---|---|
| 4,275,966 | 6/1981 | Kleesattel ................................. 356/378 |
| 5,559,173 | 9/1996 | Campo et al. . |
| 5,590,251 | 12/1996 | Takagi . |
| 5,642,192 | 6/1997 | Gordon et al. ........................... 356/328 |
| 5,650,942 | 7/1997 | Granger . |
| 5,859,708 | 1/1999 | Feldman ................................... 356/406 |

*Primary Examiner*—F. L. Evans
*Attorney, Agent, or Firm*—Marvin Snyder; Douglas E. Stoner

[57] ABSTRACT

A sample having a coined line is analyzed by traversing a light spot across the sample, and then analyzing both specular and diffuse light reflected from the sample to spatially resolve the coined line. An analyzer includes a holder for supporting the sample which is illuminated by projecting the light spot onto the sample. Light collectors receive the specular and diffuse light from the sample at the spot. The received light is analyzed to detect changes therein indicative of the coined line.

12 Claims, 2 Drawing Sheets

COINED LINE ANALYZER

BACKGROUND OF THE INVENTION

This invention relates generally to measurement devices, and, more specifically, to optical spectrometers.

Various commercial products are manufactured from plastic. In one example, plastic is used for countertops which are offered in various solid colors or patterns. Enduran (trademark) plastic is commercially available from the General Electric Company in various color patterns commonly having natural stone appearance features. For example, this plastic may have varying color for emulating natural stones such as granite or marble.

Plastic countertops used in kitchens should have sufficient strength to resist damage over a suitable life. One type of damage includes a coined line which is a physical indentation in the surface of the countertop typically formed by a sharp edge pressed along the countertop surface. A simple coined line is merely an indentation in the surface without otherwise affecting the surface pattern or color. In a worst case, a coined line becomes a physical scratch in the surface which removes a portion of the pattern or color from the underlying material.

It is therefore desirable to formulate kitchen countertops with maximum coinability resistance so that they may be used over many years without undesirable degradation in appearance. During the manufacturing process, the composition of the countertop plastic may be varied for various reasons including achieving high coinability resistance. Sample countertops may be manufactured and tested to intentionally produce a coined line therein which may then be analyzed. Presently, coined lines are merely visually observed without quantitative evaluation.

Accordingly, it is desired to provide an analyzer for detecting and quantifying the extent of a coined line in a plastic product.

BRIEF SUMMARY OF THE INVENTION

A sample having a coined line is analyzed by traversing a light spot across the sample, and then analyzing both specular and diffuse light therefrom to spatially resolve the coined line. An analyzer includes a holder for supporting the sample which is illuminated by projecting the light spot thereon. Light collectors are provided for receiving the specular and diffuse light from the sample at the spot. The light is analyzed to detect changes therein indicative of the coined line.

DETAILED DESCRIPTION OF THE INVENTION

Figure 1:
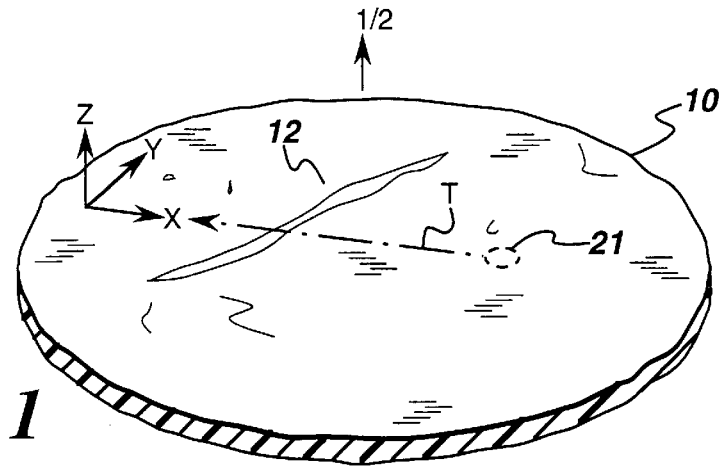
FIG. 1 is a top isometric view of a portion of a sample having a coined line therein for being spatially resolved.

FIG. 1 illustrates a portion of a plastic sheet or laminate defining a sample 10 which includes an integral pattern of any desired configuration. The pattern may vary in color intensity or shades to produce a desired appearance such as that of natural stones, for example, granite or marble. Alternatively, the sample may have a single color without pattern.

Plastic sheets are manufactured for various applications and therefore have different material compositions. The specific material composition affects resistance of the plastic sheet to coining damage. As indicated above, coining is simply the permanent or plastic deformation of the exposed surface of the plastic sheet due to a concentrated force carried along the surface. One example of the resulting coined line 12 is illustrated in FIG. 1.

In a simple form, coined line 12 is a concave indentation in the exposed surface of sample 10 which extends longitudinally for a finite length. The coined line is a local compression in the surface of the sample, with the surface pattern of the sample being otherwise unaffected. However, the coined line may be severe enough to actually scratch the sample surface and locally interrupt or destroy the continuity of the desired surface color pattern.

Accordingly, the material composition of sample 10 may be varied in its fabrication process, with coined lines 12 being intentionally formed in the material and evaluated for the coinability resistance of the corresponding sample material composition. An analyzer 14 is specifically configured to detect and quantify the extent of coined line 12, as shown schematically in FIG. 2 in accordance with an exemplary embodiment of the invention.

Coined line analyzer 14 is a system comprised of components including a holder 16 in any suitable form, such as a plate having a window or aperture 18 therethrough upon which sample 10 may be mounted for analysis. The sample may be a portion of a manufactured plastic sheet for which analysis is desired.

Disposed adjacent the aperture 18 is an illuminator 20 for projecting light 22 in a spot on the sample. A first light collector 26 is optically aligned with the holder for receiving specular light reflected from the illuminated spot on the sample. A second light collector 28 is also optically aligned with the holder for receiving diffuse light diffused from the illuminated spot on the sample.

A light analyzer or sensor 30 is optically coupled to both the first and second collectors 26 and 28, respectively, for analyzing the specular and diffuse light therefrom.

Support means in the exemplary form of a multiaxis carriage or stage 32 are provided for supporting holder 16 for selective movement along multiple axes to traverse the light spot across the sample, preferably by traversing the sample relative to the spot. In this manner, a plurality of light readings across the sample can be obtained to spatially resolve the surface pattern of the sample. Specifically, the sample may be analyzed by spatially resolving the pattern obtained by traversing light spot 22 along a line T having a plurality of discrete sites, as shown in FIG. 1. The specular and diffuse light at the several sites is then analyzed by sensor 30 to spatially resolve the coined line with quantitative data.

Figure 2:
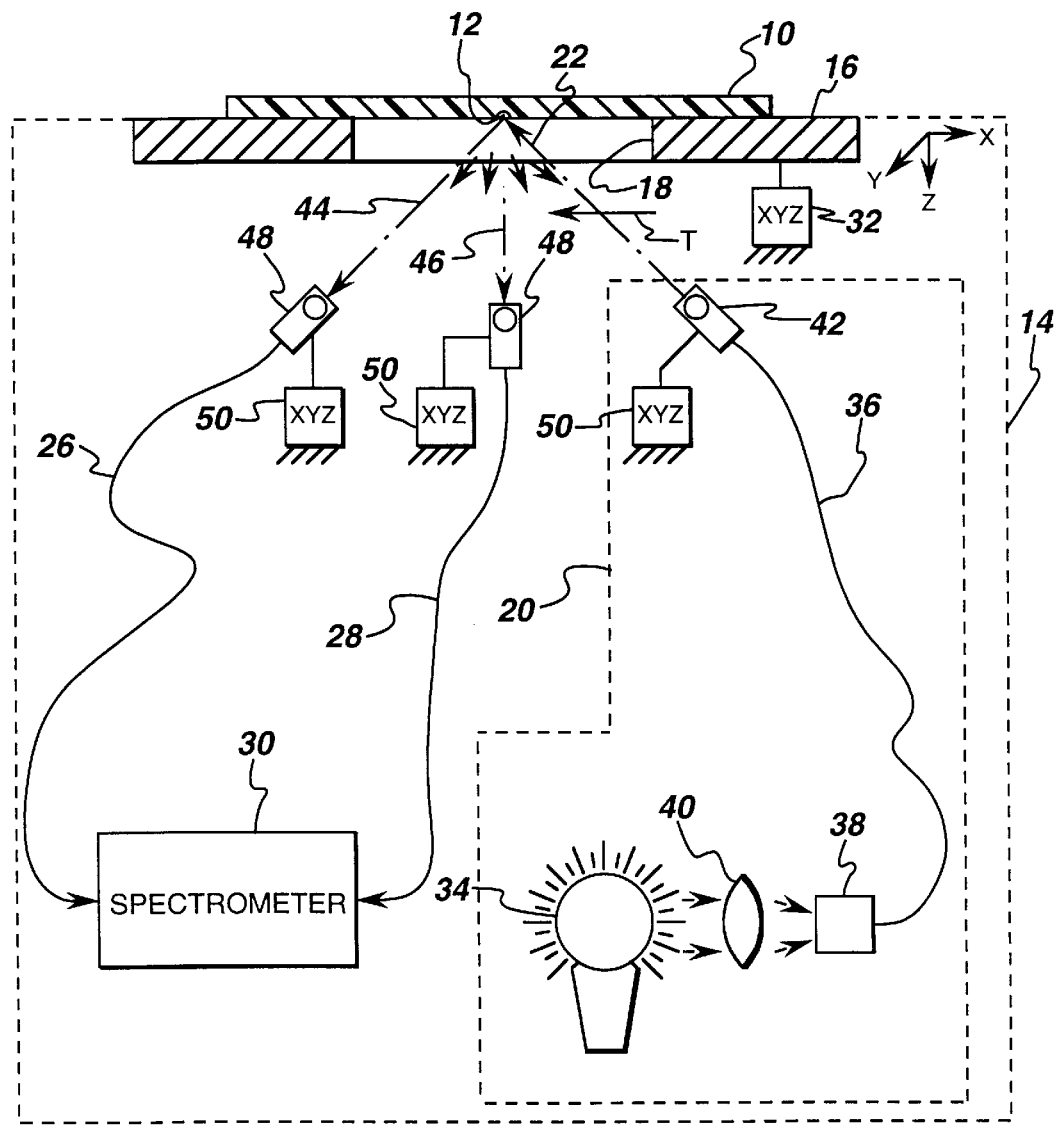
FIG. 2 is a schematic representation of a coined line analyzer for analyzing the sample illustrated in FIG. 1.

As shown in FIG. 2, illuminator 20 is comprised of components including a suitable light source or lamp 34 and a cooperating optical fiber 36 which channels light 22 from the lamp to define the spot on the sample. The projection or illumination fiber 36 includes an input end 38 optically aligned with lamp 34 through an optical focusing lens 40 for example, and also includes an output end 42 containing an integral ball lens for projecting the light spot onto the sample. Lamp 34 may comprise any conventional light source, such as a tungsten-halogen lamp with an optical wavelength of about 400–770 nm in the visible light spectrum.

Light 22 is preferably projected from illumination fiber 36 obliquely to the sample surface in the vicinity of coined line 12. The light is reflected, both specularly and diffusely, from the sample surface to produce specular light 44 and diffuse light 46.

First and second collectors 26,28 are preferably in the form of respective optical fibers each having preferably identical input ends or terminations 48 which, similar to output end 42 of the illumination fiber, contain integral ball lenses which are adjustable for reducing or enlarging the cone angle of light leaving or entering the respective fibers.

Second collection fiber 28 is optically aligned at its input end 48 with the holder between first collection fiber 26 and illumination fiber 36 at their respective terminations 48,42. Since specular light 44 is reflected from sample 10, the angular orientation of the input end of first collection fiber 26 matches the angular orientation of the output end of illumination fiber 36, both relative to the normal or perpendicular from the sample, to properly position these fibers to correspond with the equal angle of incidence and angle of reflection of the light from the sample.

The input end of second collection fiber 28 may be disposed at any suitable position, preferably perpendicularly to the sample and between the two other fibers, for receiving diffuse light 46 from the sample at the illumination spot. In this way, the different angular orientations of the first and second collection fibers are effective for receiving both specular and diffuse light from the sample independently of each other.

Light sensor 30, as illustrated in FIG. 2, is in the exemplary form of a spectrometer and may take any other conventional form for analyzing the reflected specular and diffused light 44 and 46, respectively. The sensor is configured to separately analyze specular light 44 from first collection fiber 26 and diffuse light 46 from second collection fiber 28. This light is analyzed in the spectrometer and displayed or provided in any conventional format for use in analyzing coined line 12.

Spectrometer 30, illumination fiber 36, collection fibers 26,28, and associated terminals or end fittings are all commercially available from Ocean Optics, Inc., of Dunedin, Fla. Other conventional equipment may alternatively be used.

In the preferred embodiment illustrated in FIG. 2, main stage 32 supporting the holder and sample has three axes of translation movement or adjustment X,Y,Z, and two axes of rotation adjustment to level the sample. Similarly, output end 42 of illumination fiber 36 is supported by a similar multiaxis ministage 50 which also provides three axes of adjustment X,Y,Z. Input ends 48 of collection fibers 26,28 also include corresponding multiaxis ministages 50 for providing three axes of adjustment in X,Y,Z directions.

The three fibers 26,28,36 are preferably mounted directly below holder 16 for maintaining a constant offset distance from the bottom of sample 10 resting atop holder 16. In this way, the thickness of the sample does not affect the distance between the analyzed down-facing surface of the sample which is maintained at a constant vertical distance above the fiber ends once positional adjustments have been made.

In operation, the light generated by lamp 34 is channeled through illumination fiber 36 to produce a narrow light spot 21 at a corresponding analysis site on the sample, shown in FIG. 1. The specular and diffuse light is collected by the input fibers and delivered to spectrometer 30 wherein it is analyzed in any conventional format such as the L,a,b color format indicative of intensity, red-green shift, and yellow-blue shift, respectively. Corresponding L,a,b data are then obtained in turn at each of the several analysis sites along the traversed line T.

The spatial data may be obtained by operating holder stage 32 to produce a suitable line of sites over a finite area of the sample for analyzing the coined line thereon. Sample 10 is preferably traversed linearly along the X-axis, for example, to produce a suitable number of corresponding analysis sites.

Figure 3:
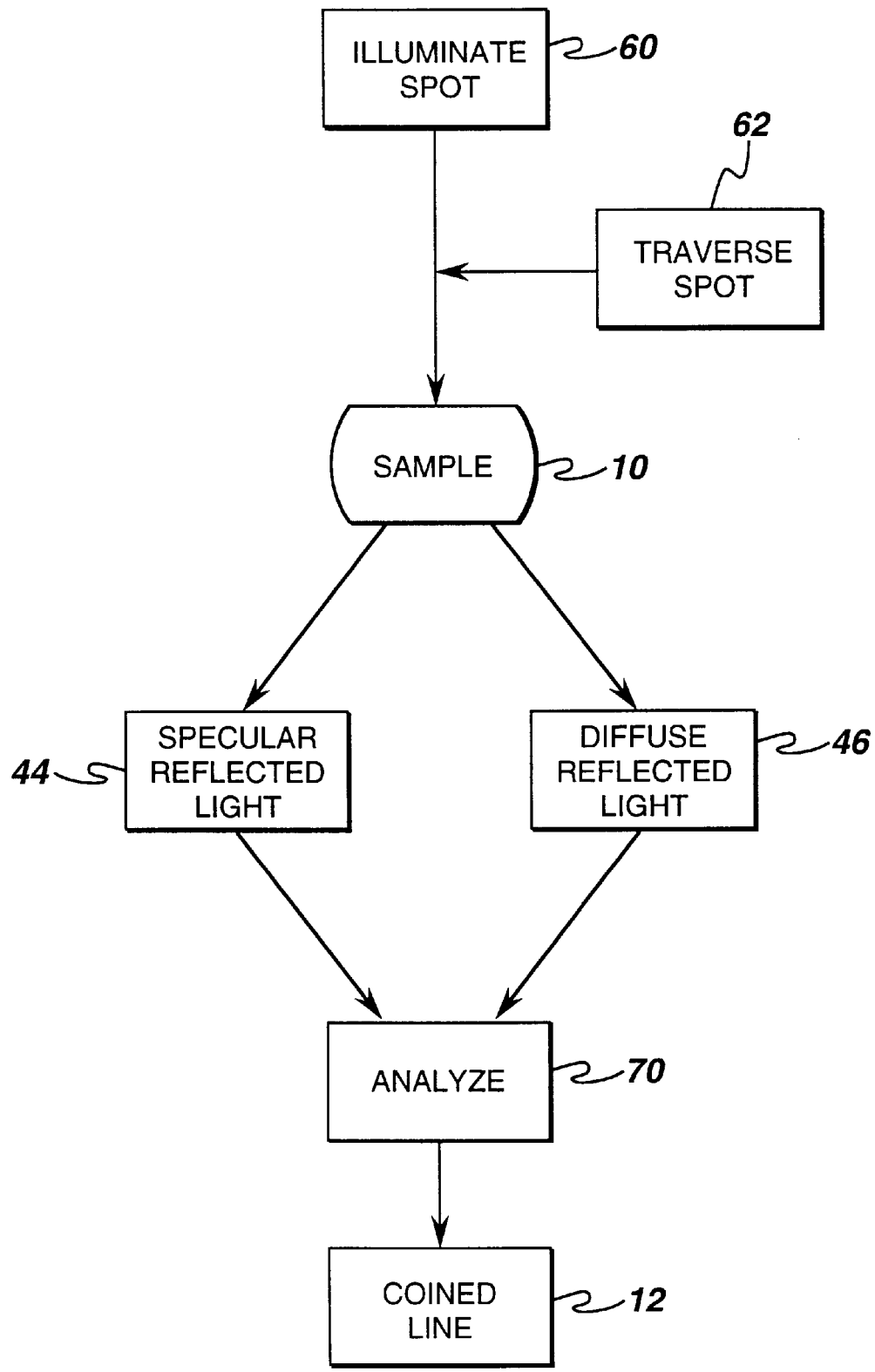
FIG. 3 is a flowchart representation of a method of analyzing the coined line sample illustrated in FIGS. 1 and 2.

FIG. 3 illustrates schematically a method for analyzing coined line 12 illustrated in FIGS. 1 and 2 in accordance with an exemplary embodiment of the present invention. Main stage 32 may be operated to traverse light spot 21 across sample 10 for obtaining a suitable number of discrete analysis sites from which corresponding L,a,b data are obtained and suitably stored. Alternatively, holder 16 may be held fixed and analyzer 14 operated to traverse light spot 21 across the sample to obtain the discrete analysis sites. In either instance, the L,a,b data for the several analysis sites are indicative of coined line 12 in the area traversed.

As indicated in FIG. 3, spot 21 is illuminated with light at step 60, and light spot 21 is traversed across sample 10 at step 62 by operating holder stage 32. Specular light 44 and diffuse light 46 reflected from the surface of sample 10 are analyzed at step 70 to quantify the surface coining.

More specifically, spectrometer 30 may be used for analyzing both specular and diffuse light reflected from the sites to spatially resolve coined line 12 in a quantitative manner. This may be accomplished in different combinations of the specular and diffuse reflected light.

The specular and diffuse reflected light are preferably analyzed for detecting changes therein transversely across coined line 12. Changes in the specular light may be analyzed independently of changes in the diffuse light. Alternatively, changes in the diffuse light may be analyzed independently of changes in the specular light. As another alternative, changes in both the specular and diffuse light may be analyzed simultaneously for evaluating the extent of coined line 12.

Since coined line 12, as illustrated in FIG. 2, is a surface irregularity of the sample, it will reflect specular and diffuse light differently than the surrounding portions of the sample which are relatively uniform in appearance and surface finish. As light spot 21 traverses the sample from the smooth surface over coined line 12, the detected specular and diffuse light correspondingly change in intensity at the corresponding collection fibers 26,28, which is indicative of the presence of the coined line.

The specular light is indicative of changes in surface geometry, such as dents, and surface finish, such as gloss or matte. The diffuse light is indicative of surface color changes. Accordingly, both the specular and diffuse light may be analyzed together to quantify the surface coining.

The depth, width, and surface irregularity of the coined line determines the changes in the specular and diffuse light as the illumination light spot is traversed across the line. The resulting data from spectrometer 30 may then be suitably calibrated for providing a quantitative indication of the extent of coined line 12.

For example, a series of reference coined lines varying in width, depth, and surface irregularity may be created and then analyzed using analyzer 14 for obtaining reference values indicative of the change in the specular and diffuse light upon traversing the coined lines. These reference values may then be used for quantifying the degree of coined line deformation in a sample in order to evaluate the coinability resistance of the specific material composition being evaluated. Accordingly, analyzer 14 constitutes a convenient apparatus for providing a quantitative indication of coined lines in various workpieces.

While only certain preferred features of the invention have been illustrated and described, many modifications and changes will occur to those skilled in the art. It is, therefore, to be understood that the appended claims are intended to cover all such modifications and changes as fall within the true spirit of the invention.

We claim:

1. An analyzer for a sample having a coined line comprising:

an illuminator for projecting a light spot on said sample;

a first light collector for receiving specular light reflected from said sample at said spot;

a second light collector for receiving diffuse light reflected from said sample at said spot;

a light sensor optically coupled to both said first and second collectors for analyzing said specular and diffuse light; and means for traversing said spot across said sample for obtaining a plurality of light readings thereacross to spatially resolve said coined line.

2. An analyzer according to claim 1 wherein said illuminator comprises:

a light source; and an optical illumination fiber having an input end optically aligned with said light source, and an output end for projecting said light spot onto said sample.

3. An analyzer according to claim 2 wherein said first and second collectors comprise respective first and second optical fibers.

4. An analyzer according to claim 3 wherein said second fiber is situated between said first fiber and said illumination fiber for receiving diffuse light reflected from said sample at said spot at a different orientation than orientation of said first fiber for receiving said specular light.

5. An analyzer according to claim 4 wherein said light sensor comprises a spectrometer configured to separately analyze said specular light from said first fiber and said diffuse light from said second fiber.

6. An analyzer according to claim 1 including a holder for supporting said sample.

7. An analyzer according to claim 6 wherein said holder and said illuminator are adapted to move relative to each other.

8. A method of analyzing a sample having a coined line therein, comprising the steps of:

traversing a light spot across a plurality of sites along said sample including said coined line; and analyzing both specular and diffuse light reflected from said sites to spatially resolve said coined line.

9. A method according to claim 8 wherein the step of analyzing both specular and diffuse light further comprises detecting changes in said sites across said coined line.

10. A method according to claim 8 wherein the step of analyzing both specular and diffuse light further comprises analyzing said specular light to detect changes therein, independently of changes in said diffuse light.

11. A method according to claim 8 wherein the step of analyzing both specular and diffuse light further comprises analyzing said diffuse light to detect changes therein, independently of changes in said specular light.

12. A method according to claim 8 wherein the step of analyzing both specular and diffuse light further comprises analyzing said specular and diffuse light to detect simultaneous changes therein.

* * * * *